United States Patent [19]

Butler

[11] 4,229,457
[45] Oct. 21, 1980

[54] 3-(3-SUBSTITUTED ARYLOXY)-2-YRIDINECARBONITRILES, PHARMACEUTICAL COMPOSITIONS AND METHODS FOR THEIR PRODUCTION

[75] Inventor: Donald E. Butler, Ann Arbor, Mich.

[73] Assignee: Warner-Lambert Company, Morris Plains, N.J.

[21] Appl. No.: 79,408

[22] Filed: Sep. 27, 1979

Related U.S. Application Data

[62] Division of Ser. No. 960,212, Nov. 13, 1978, abandoned.

[51] Int. Cl.³ .............................................. A61K 31/44
[52] U.S. Cl. .................................... 424/263; 546/288; 546/300
[58] Field of Search ......................... 424/263; 546/288

[56] References Cited

U.S. PATENT DOCUMENTS

| | | | |
|---|---|---|---|
| 4,187,311 | 2/1980 | Butler | 424/263 |
| 4,187,379 | 2/1980 | Butler | 546/288 |

OTHER PUBLICATIONS

Villani et al., Journal of Medicinal Chemistry, vol. 18, No. 1, pp. 1-9, (1975).

*Primary Examiner*—Alan L. Rotman
*Attorney, Agent, or Firm*—Stephen Raines; Albert H. Graddis; Frank S. Chow

[57] ABSTRACT

New 3-(3-methoxyphenoxy)-2-pyridinecarbonitriles, which are useful as pharmacological agents, especially as agents for the treatment of senility and reversal of amnesia, are disclosed. Other known 3-(3-substituted phenoxy)-2-pyridinecarbonitriles are disclosed having the same utility. The compounds can be produced by dehydrating the appropriately substituted oxime or displacing an alkoxy group to give the desired carbonitrile.

2 Claims, No Drawings

3-(3-SUBSTITUTED ARYLOXY)-2-YRIDINECARBONITRILES, PHARMACEUTICAL COMPOSITIONS AND METHODS FOR THEIR PRODUCTION

SUMMARY AND DETAILED DESCRIPTION

This is a division of application Ser. No. 960,312 filed Nov. 13, 1978.

The present invention relates to new 3-(3-methoxyphenoxy)-2-pyridinecarbonitrile compounds. More particularly, the invention relates to a compound of the formula

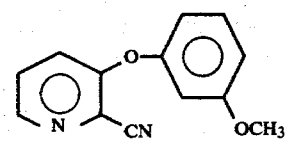

I and pharmaceutically-acceptable acid addition salts thereof.

In addition, the ivention is directed to pharmaceutical compositions comprising compounds of the formula

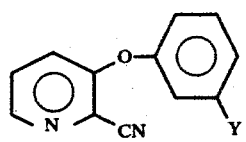

II and pharmaceutically-acceptable acid addition salts thereof wherein Y is methoxy, methyl, fluoro or chloro.

The term "pharmaceutically-acceptable acid addition salts" is intended to mean a relatively non-toxic salt, such as the salt formed by employing the following acids; hydrochloric acid, sulfuric acid, acetic acid, citric acid, etc.

In accordance with the invention, the foregoing compounds of formula II can be prepared by reacting a compound of the formula

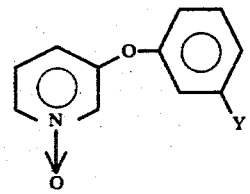

III wherein Y is as previously defined, with an alkylating agent, such as dimethylsulfate, diethylsulfate, trimethyloxonium tetrafluoroborate, triethyloxonium tetrafluoroborate, methylbromide or methyliodide; preferably dimethylsulfate; followed by treatment with an alkali metal cyanide, preferably sodium cyanide. Prior to the addition of the alkali metal cyanide an intermediate compound is formed, which is not isolated, having the structure

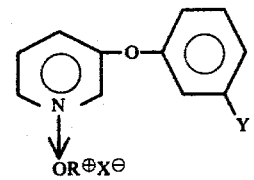

IV where $R^\oplus$ is a carbonium ion derived from the alkylating agent. The pharmaceutically-acceptable salts are prepared by adjusting the pH.

The first step is conducted preferably in the absence of solvent, although a halogenated hydrocarbon may be employed (dichloromethane, tetrachloroethane or dichlorobenzene). The reactants are present in about equimolar amounts although a slight excess of alkylating agent is preferred.

The first step of the reaction is carried out at a temperature range of 25° C. to 100° C. for periods of from one to 10 hrs, preferably 95° to 100° C. for from three to four hrs.

The second step is carried out in water in an inert atmosphere using an excess of alkali metal cyanide.

The second step of the reaction is carried out at a temperature range of −5° C. to 30° C. for periods of from one to 24 hours, preferably −5° C. to 5° C. for periods of from four to six hours.

The product may be isolated as the free base by distillation or crystallization or as an acid addition salt by suitable adjustment of pH.

The necessary starting material of formulae III is a known compound.

A second process for the preparation of compounds of the invention or compounds used in the pharmaceutical compositions of the invention requires the treatment of a compound of the formula

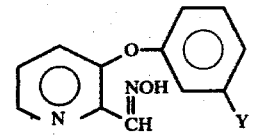

V wherein Y is as previously defined, with a dehydrating agent. The product may be isolated in the form of a free base or treated with the appropriate acid to give rise to the desired acid-addition salt.

An excess of a dehydrating agent, such as thionyl chloride, phosphorus pentachloride, phosphorus oxychloride, acetic anhydride may be used, preferably thionyl chloride and a relatively inert organic solvent such as a chlorinated hydrocarbon (dichloromethane, tetrachloroethane, o-dichlorobenzene, etc.) or aromatic compound (benzene, toluene, etc.)

The reaction is carried out at a temperature range of 25° C. to 120° C. for periods of from one-half to 16 hrs, preferably 90° C. to 110° C. for about two hrs to eight hrs.

The product may be isolated by distillation or crystallization and converted to the appropriate acid-addition salt.

The compounds of the invention may exist in anhydrous form as well as in solvated, including hydrated, forms. In general, the hydrated forms and the solvated forms with pharmaceutically-acceptable solvents are equivalent to the anhydrous or unsolvated form for the purposes of the invention.

Also in accordance with the invention, pharmaceutical compositions may be produced by formulating the compounds of formula II in dosage unit form with a pharmaceutical carrier. Some examples of dosage unit forms are tablets, capsules, lozenges, and pills; as well as powders and aqueous and non-aqueous solutions and suspensions packaged in containers containing either one or some larger number of dosage units and capable of being sub-divided into individual doses by such means as measurement into teaspoon or other standard container. Some examples of suitable pharmaceutical carriers, including pharmaceutical diluents, are gelatin capsules; sugars such as lactose and sucrose; starches such as corn starch and potato starch; cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol; glycerine, sorbitol; polyethylene glycol; water; agar; alginic acid; as well as other compatible substances normally used in pharmaceutical formulations. The compositions of the invention can also contain other components such as coloring agents, flavoring agents, and/or preservatives. These materials, if present, are usually used in relatively small amounts. The compositions can, if desired, also contain other therapeutic agents.

The percentage of the active ingredient in the foregoing compositions can be varied within wide limits but for practical purposes it is preferably present in a concentration of at least 10% in a solid composition and at least 2% in a primarily liquid composition. The most satisfactory compositions are those in which a much higher proportion of the active ingredient is present. The compositions of the invention preferably contain from 1 to 500 mg, preferably 5 to 100 mg of the active ingredient per dosage unit so that the entire amount to be administered during a day can be made up from a reasonable number of dosage units.

The compounds of formula II may be incorporated into formulations intended for parenteral administration. Such compositions may be in a powdered form intended to be combined with an isotonic solution containing other ingredients such as preservatives, etc. or may be initially formulated as part of an isotonic solution which may contain preservatives, other active ingredients, etc.

The compounds of the invention are new chemical compounds of value as pharmacological agents. More specifically, they are agents which are potentially useful in treating patients suffering from senility. The compounds also find use in the treatment of induced amnesia. The compounds of the invention generally would be administered to mammals in a dosage range of from about 0.014 to about 21.4 mg per kg of body weight per day, preferably 0.36 to 10.7 mg per kg per day. Thus 1 mg to 1500 mg, preferably 25 mg to 750 mg, are administered to a 70 kg host per day.

The effectiveness of the aforementioned compounds is determined by the following test. This test is designed to show the compound's ability to reverse amnesia produced by electroconvulsive shock.

One hundred male mice (Carworth, CF-1 strain, 19–21 g at time of shipment) are divided into five groups of 20 mice each. Each mouse is placed, one at a time, on a small shelf attached to the outside wall of a test box. In this position the mouse is suspended in space. Therefore, the mouse is motivated to step from the shelf through a conveniently placed small hole into the interior of the box. As soon as the mouse has all four feet within the semidarkened interior of the box, the grid floor of the box is electrified (1.5 milliamps, 3 second duration) to produce a strong pain-fear reaction from the animal. About five seconds thereafter, the mouse is removed from the test box and placed in a group holding cage.

Two hours after the above training the mice are given a single electroconvulsive shock produced by 20 milliamps delivered for 0.5 seconds through the ears. Immediately thereafter, the mice are returned to the holding cage.

Two hours after the convulsive treatment, the mice are injected intraperitoneally with the chemical being assesed. Usually three doses of the chemical will be tested at a time.

One hour after the drug treatment, the mice are tested for memory of the painful foot shock received within the self-box apparatus. This testing is accomplished by once again placing each mouse on the small shelf attached to the test box. Any mouse that stays on the shelf for 60 seconds without entering the box is counted as remembering the painful foot shock received within the box five hours earlier. Any mouse entering the box within the 60-second period is counted as having amnesia for the painful event.

Using this 60-second criterion, appropriate control experiments show (1) 100 percent of mice will enter the box if no foot shock is delivered during the original training, (painful foot shock is necessary if the mice are to develop an aversion to entering the test box) (2) 100 percent of mice will enter the box under the foregoing conditions even when treated with electroconvulsive shock at the three-hour point prior to testing (electroconvulsive shock treatment itself does not generate a fear of entering the test box).

The five groups of mice are treated as follows:

| Group | |
|---|---|
| (1) Ceiling Control Group: | Placebo |
| (2) Base Line Control Group: | Electroconvulsive shock, Placebo |
| (3) 1st Drug Dose Group: | Electroconvulsive shock, 3-(3-substituted aryloxy)-2-pyridinecarbonitrile or salt thereof |
| (4) 2nd Drug Dose Group: | Electroconvulsive shock, 3-(3-substituted aryloxy)-2-pyridinecarbonitrile or salt thereof |
| (5) 3rd Drug Dose Group: | Electroconvulsive shock, 3-(3-substituted aryloxy)-2-pyridinecarbonitrile or salt thereof |

The percentage of amnesia reversal is determined as follows for each drug group:

$$\text{Percent amnesia reversal} = \frac{\text{Drug group} - \text{Base line control group}}{\text{Ceiling control group} - \text{Base line control group}} \times 100$$

The following criteria is used in interpreting the percent of amnesia reversal scores:

40 percent or more (active=A) 25 to 39 percent (borderline=C) and 0 to 29 percent (inactive=N). The duration of the electroconvulsive shock can be varied making the test more or less difficult for a compound to demonstrate an A or C rating. Thus a compound with activity in senile patients and in patients with early memory defects, Piracetam ® [Acta Psychiat. Scand. 54, 150 (1976)], has been administered in this test using the above methodology and 0.2 second and 0.5 second electroconvulsive shock and gave the following results.

| Piracetam ® (mg/kg) | 0.2 sec ECS | 0.5 sec ECS |
|---|---|---|
| 80 | C | N |
| 20 | A | N |
| 5 | C | N |

The inverted U shaped dose response curve is typical of this type of agent.

The following table reports the results for certain compounds of the invention:

TABLE 1

| Compound | LMC test Dose levels (mg/kg) | | | | | | |
|---|---|---|---|---|---|---|---|
| | 1.25 | 2.5 | 5.0 | 20. | 40. | 80. | 160. |
| Example 1 | C | C | A | A | C | A | N |
| 2 | | | N | A | | A | |

The invention is illustrated by the following examples.

EXAMPLE 1

3-(3-Methoxyphenoxy)-2-pyridinecarbonitrile

A solution of 68 g of 3-(3-methoxyphenoxy)pyridine in 100 ml of glacial acetic acid is treated with 75 g of 40% peracetic acid in acetic acid. The mixture is stirred 16 hours at 35° C. and then is refluxed 1 hour. The mixture is cooled, 100 ml isopropanol added, and the mixture is concentrated at reduced pressure. The oily residue is dissolved in 500 ml of dichloromethane and is washed with excess cold 25% sodium hydroxide solution. The organic layer is concentrated to yield 3-(3-methoxyphenoxy)pyridine 1-oxide, m.p. 75°–77° C.

A melt of 63 g of 3-(3-methoxyphenoxy)pyridine N-oxide is held at 95° C. and 40 g of dimethyl sulfate is added dropwise. The mixture is stirred at 105° C. for 4 hours to yield 1-methoxy-3-(3-methoxyphenoxy)-pyridinium methosulfate. This is dissolved in 100 ml water and is added dropwise to a solution of 100 g of sodium cyanide in 200 ml of water held at 0°–5° C. with stirring under a nitrogen atmosphere. The mixture is stirred 18 hours and is extracted with 500 ml of chloroform. The chloroform solution is dried, concentrated and distilled to yield 2-cyano-3-(3-methoxyphenoxy)-pyridine; b.p. 125°–130° C. at 0.2 min, m.p. 112°–114° C. after recrystallization from isopropanol.

EXAMPLE 2

3-(3-Fluorophenoxy)-2-pyridinecarbonitrile

A solution of 32 g of 3-(3-fluorophenoxy)pyridine [Fr. Pat. No. 1,472,619 (1967)] in 50 ml of glacial acetic acid is treated with 35 g of 40% peracetic acid in acetic acid and the mixture is refluxed 16 hours. The mixture is concentrated at reduced pressure and the oil is dissolved in 250 ml of dichloromethane. The dichloromethane solution is washed with excess 10% sodium hydroxide solution. The solution is dried and concentrated to dryness to yield 3-(3-fluorophenoxy)pyridine 1-oxide, m.p. 63°–66° C.

By substituting 58 g of 3-(3-fluorophenoxy)pyridine 1-oxide for the 3-(3-methoxyphenoxy)pyridine 1-oxide in Example 1, the product is 3-(3-fluorophenoxy)-2-pyridinecarbonitrile, m.p. 82°–85° C. after recrystallization from isopropanol.

EXAMPLE 3

Pharmaceutical Composition containing 3-(3-methoxyphenoxy)-2-pyridinecarbonitrile

| Ingredient | Quantity |
|---|---|
| 3-(3-Methoxyphenoxy)-2-pyridinecarbonitrile | 150 g |
| Lactose | 1038 g |
| Corn Starch | 39 g |
| Hydroxypropyl cellulose | 30 g |
| Magnesium stearate | 7 g |
| Ethanol-water 50:50 | qs |

The 3-(3-methoxyphenoxy)-2-pyridinecarbonitrile, lactose and hydroxypropyl cellulose are blended and granulated with 50:50 ethanol water. The wet granulation is screened, dried and re-screened. The resulting dried granulation is blended with the magnesium stearate and the corn starch, and the mixture is compressed into 225 mg tablets using 11/32 inch standard concave punches. Yield equals approximately 6,000 tablets each containing 25 mg of 3-(3-methoxyphenoxy)-2-pyridinecarbonitrile.

I claim:

1. A pharmaceutical composition for treating senility comprising an effective amount of compound of the formula

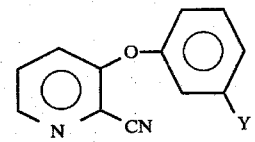

and pharmaceutically-acceptable salts thereof wherein Y is methoxy, methyl, chloro or fluoro and a pharmaceutical carrier.

2. A method for treating senility which comprises administering to a patient in need of such treatment an effective amount of the composition of claim 1.

* * * * *